United States Patent
Nelagadde

(10) Patent No.: US 10,101,252 B2
(45) Date of Patent: *Oct. 16, 2018

(54) METHOD OF MEASURING DAMPING USING OPTICAL IMAGING TECHNIQUE

(75) Inventor: Manoj Nelagadde, Canton, MI (US)

(73) Assignee: RASSINI FRENOS, S.A. DE C.V., San Martin Texmelucan (MX)

( * ) Notice: Subject to any disclaimer, the term of this patent is extended or adjusted under 35 U.S.C. 154(b) by 674 days.

This patent is subject to a terminal disclaimer.

(21) Appl. No.: 13/825,376

(22) PCT Filed: Sep. 23, 2011

(86) PCT No.: PCT/US2011/052999
§ 371 (c)(1),
(2), (4) Date: Nov. 14, 2014

(87) PCT Pub. No.: WO2012/040584
PCT Pub. Date: Mar. 29, 2012

(65) Prior Publication Data
US 2015/0062330 A1     Mar. 5, 2015

Related U.S. Application Data

(60) Provisional application No. 61/386,098, filed on Sep. 24, 2010.

(51) Int. Cl.
*H04N 7/18* (2006.01)
*G01N 3/30* (2006.01)
*G01M 7/08* (2006.01)

(52) U.S. Cl.
CPC ............... *G01N 3/30* (2013.01); *G01M 7/08* (2013.01); *G01N 2203/0039* (2013.01); *G01N 2203/0647* (2013.01); *G01N 2203/0688* (2013.01)

(58) Field of Classification Search
None
See application file for complete search history.

(56) References Cited

U.S. PATENT DOCUMENTS

| | | |
|---|---|---|
| 3,383,980 A | 5/1968 | Richter |
| 5,347,190 A | 9/1994 | Lewis et al. |
| 5,351,951 A * | 10/1994 | Hodgetts ............... A63B 60/42 473/289 |

(Continued)

FOREIGN PATENT DOCUMENTS

| | | |
|---|---|---|
| CN | 100371619 C | 2/2008 |
| CN | 101178349 A | 5/2008 |

(Continued)

OTHER PUBLICATIONS

Svend Gade et al.; "Digital Filter Techniques vs. FFT Techniques for Damping Measurements (Damping Part I)"; Technical Review, No. 1-1994; Dec. 31, 2004; 5 pages.

(Continued)

Primary Examiner — Dakshesh D Parikh
(74) Attorney, Agent, or Firm — Cantor Colburn LLP

(57) ABSTRACT

A method includes exciting a work piece, measuring a dynamic response of the work piece with an optical imaging system and calculating a damping factor and a Q factor from said dynamic response. The method links two processes: an optical imaging system to output dynamic motion response data, and using the data to obtain a damping factor and a Q factor.

7 Claims, 5 Drawing Sheets

(56) References Cited

U.S. PATENT DOCUMENTS

| | | | |
|---|---|---|---|
| 6,014,899 | A | 1/2000 | Uhlig et al. |
| 6,314,813 | B1 | 11/2001 | Uhlig |
| 6,370,958 | B1 | 4/2002 | Uhlig |
| 6,382,027 | B1 | 5/2002 | Uhlig |
| 6,489,776 | B1 | 12/2002 | Stowe et al. |
| 6,505,716 | B1* | 1/2003 | Daudi .............. B23H 9/00 188/250 B |
| 2007/0113678 | A1* | 5/2007 | Baker .............. G01F 1/8413 73/861.357 |
| 2009/0312966 | A1* | 12/2009 | Nobis .............. G01M 17/04 702/56 |
| 2010/0307248 | A1 | 12/2010 | Hayashi |
| 2015/0085107 | A1 | 3/2015 | Nelagadde |

FOREIGN PATENT DOCUMENTS

| | | |
|---|---|---|
| DE | 102006039536 A1 | 3/2008 |
| JP | 2000321016 A | 11/2000 |
| KR | 1020110021271 A | 3/2011 |
| KR | 1020120032895 A | 4/2012 |
| WO | 2009069670 A1 | 4/2011 |
| WO | 2012040584 A1 | 3/2012 |

OTHER PUBLICATIONS

Y.F. Ji et al.; "Nontarget Stereo Vision Technique for Spatiotemporal Response Measurement of Line-Like Structures"; Journal of Engineering Mechanics; vol. 134, No. 6; Jun. 2008; pp. 466-474.

Chinese Office Action for related Chinese Application No. 201180051363.2 dated Sep. 26, 2014; 13 pages.

International Search Report for International Application No. PCT/US2013/037788; International Filing Date Apr. 23, 2013; 5 pages.

Written Opinion for International Application No. PCT/US2013/037788; International Filing date Apr. 23, 2013; 7 pages.

International Search Report; International Application No. PCT/US2011/052999; International Filing Date: Sep. 23, 2011; Date of Mailing: Jan. 17, 2012, 6 pages.

Written Opinion of International Searching Authority; International Application No. PCT/US2011/052999; International Filing Date: Sep. 23, 2011; Date of Mailing: Jan. 17, 2012, 4 pages.

Office Action regarding related EP App. No. 11 827 617.9; dated Jan. 26, 2016; 8 pgs.

N. Thrane, J. Wismer, H. Konstantin-Hansen and S. Gade, "Application Note: Practical use of the 'Hilbert transform'", Bruel & Kjaer, Dec. 1995, 2 pages.

Svend Gade and Henrik Herlufsen, "Digital Filter vs FFT Techniques for Damping Measurements", Sound and Vibration, Mar. 1990, pp. 24-31.

English Translation of Korean Office Action for related Korean Application No. 10-2013-7010219, dated Apr. 21, 2014, 3 pages.

English Translation of Mexican Office Action for related Mexican Application No. MX/a/2013/003404, dated Apr. 24, 2014, 2 pages.

Extended European Search Report for related European Application No. 11827617.9, dated Feb. 18, 2014, 11 pages.

Korean Office Action for related Korean Application No. 10-2013-7010219, dated Apr. 21, 2014, 4 pages.

Mexican Office Action for related Mexican Application No. MX/a/2013/003404, dated Mar. 13, 2014, 3 pages.

Y.F. Ji and C.C. Chang, "NonTarget Stereo Vision Technique for Spatiotemporal Response Measurement of Line-Like Structures", Journal of Engineering Mechanics, vol. 134, No. 6, Jun. 1, 2008, pp. 466-474.

Svend Gade and Henrik Herlufsen, "Digital Filter Techniques vs. FFT Techniques for Damping Measurements (Damping Part I)", Bruel & Kjaer, Dec. 1994, 42 pages.

International Preliminary Report on Patentability for International Application No. PCT/US2011/052999; Dated: Apr. 4, 2013; 5 pages.

Krupka, R., et al., "New Techniques and Applications for 3D-Brake Vibration Analysis," SAE Technical Paper Series, reprinted from Proceedings of the 18th Annual Brake Colloquium & Engineering Display, Oct. 2000; 4 pgs.

* cited by examiner

DAMPING CALCULATION FROM MOTION DECAY

METHOD OF MEASURING DAMPING USING OPTICAL IMAGING TECHNIQUE

CROSS-REFERENCES TO RELATED APPLICATIONS

This application claims priority to International Application No. PCT/US2011/052999, filed Sep. 23, 2011 and claims priority to U.S. Provisional Patent Application Ser. No. 61/386,098, filed Sep. 24, 2010, in United States Patent and Trademark Office, which is incorporated herein by reference in its entirety.

BACKGROUND OF THE INVENTION

The following description relates to a method of measuring damping of a work piece, and in particular, a method of measuring damping using a high speed camera or cameras.

Damping generally relates to the ability of a part to absorb energy when excited. Damping may be measured using a factor called a Q factor. A damping measurement may be used to assess vehicle brake noise propensity and provide a useful comparison to determine work piece vibration by capturing the ability of the work piece to absorb unwanted vibration energy. Damping measurements may be referred to using different terminology including, for example, damping factor, damping ratio, quality factor ("Q factor"), loss factor, tan delta, and/or specific damping capacity.

Current methods of damping measurement may involve exciting a part using an excitation device. An excitation device may include, for example, an impulse hammer or a shaker. Damping may be measured after the excitation device, such as the impulse hammer, strikes the work piece or part. A time and/or frequency response is then recorded using a sensor, such as an accelerometer and/or microphone. This data is processed to obtain a Q factor, which may also be referred to as a damping number. Since the damping number (Q factor) is dependent on the location on the work piece where the impulse hammer strikes, location of measurement on a brake rotor, and the frequency of vibration, it takes multiple measurements at different areas on the work piece to arrive at an optimum location to extract the numbers used to determine the Q factor. This type of iterative process of measuring may take an unsuitable period of time to complete. For example, the iterative process may take three or four minutes. In a production or lab environment, the delay due to measuring time may cause other delays. In order to reduce the measurement time, measurements may be made at multiple locations simultaneously. However, this requires a large number of sensors to be placed at or near the rotor. This increases the number of measurement channels needed.

Accordingly, it is desirable to measure damping during a reduced time period while using a limited number of sensors.

SUMMARY OF THE INVENTION

In one general aspect, there is provided a method of measuring damping of a work piece. The method includes exciting the work piece, measuring a dynamic response of the work piece with an optical imaging system, and calculating a damping factor and Q factor from the dynamic response.

In another general aspect, there is provided a method of measuring damping of a work piece including placing a work piece on a measurement surface, placing a high-speed camera to view the work piece, exciting the work piece with an excitation device and recording a displacement time history of the work piece for a predetermined amount of time. The method further includes extracting a displacement response time history of selected points on a surface of the work piece, determining a frequency of selected vibration modes, applying a filter on the time data to extract a response of modes used for a damping factor and a Q factor calculation, and calculating a damping factor and a Q factor.

These and other advantages and features will become more apparent from the following description taken in conjunction with the drawings.

BRIEF DESCRIPTION OF THE DRAWINGS

The subject matter which is regarded as the invention is particularly pointed out and distinctly claimed in the claims at the conclusion of the specification. The foregoing and other features, and advantages of the invention are apparent from the following detailed description taken in conjunction with the accompanying drawings in which:

DETAILED DESCRIPTION

Figure 1:
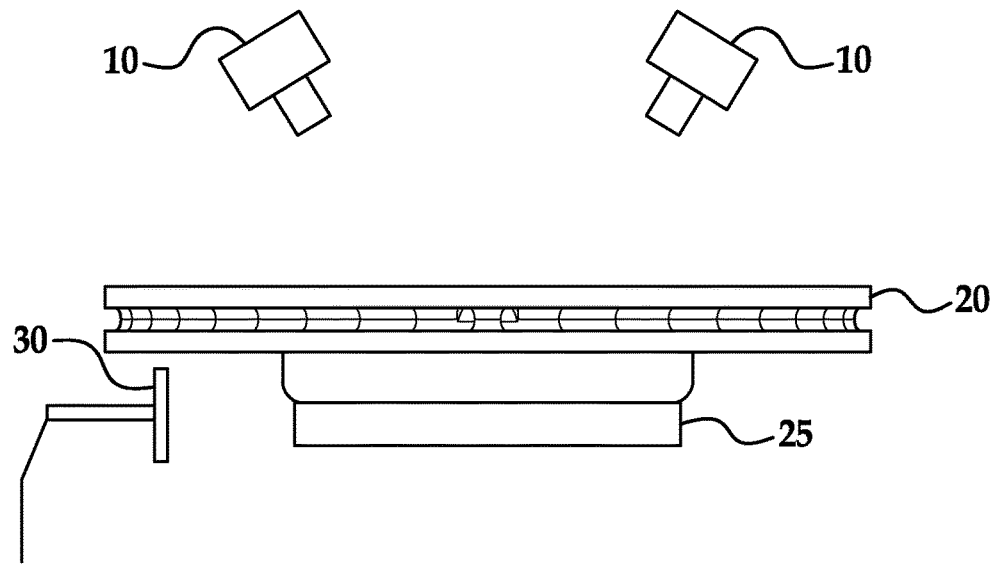
FIG. 1 illustrates an example of a set-up for measuring the dynamic response of rotor with high-speed camera.

Referring now to the Figures, where the invention will be described with reference to specific embodiments, without limiting same, and in accordance with an exemplary embodiment of the invention, FIG. 1 shows a high speed camera 10 is used to capture the dynamic motion of the work piece 20. The captured dynamic motion may include, among other things, a vibration of the work piece in response to excitation.

In an exemplary embodiment, the work piece 20 may be a brake rotor during a vibration test. For the purposes of example, the following description refers to the work piece 20 as being a brake rotor. However, it is understood that this example is non-limiting, and the work piece may also be, for example, a brake drum or other component. The high speed camera 10 captures the vibration after the brake rotor 20 is struck with an excitation device 30 and this data is used to determine the damping in the material of the brake rotor 20 at different frequencies. For the purposes of example, the following description refers to the excitation device 30 as being an impulse hammer. However, it is understood that this example is non-limiting, and the excitation device may also be, for example, a shaker or similar device. In addition, the excitation device 30 may refer to an external component or system which acts to excite the work piece 20 during operation. That is, an operational condition may cause a dynamic response in the work piece 20. For example, engine vibration or suspension vibration in a vehicle may cause a dynamic response in the work piece 20. It is understood that the examples of operational conditions above are non-limiting, and that other operational conditions may contribute to a dynamic response of the work piece 20.

By using the high speed camera 10 to record the brake rotor 20 vibration in one measurement, i.e., a single operation, it has been found that the dynamic response of any point on the brake rotor 20 may be determined and be used to obtain dynamic motion response data. The dynamic motion response data, when further processed as described herein, is used to calculate, for example, a Q factor and/or a damping factor, which may be used to measure the damping of the brake rotor 20.

The high speed camera 10 takes pictures of the brake rotor 20 at different instances of time. The information resulting from the pictures, i.e. the dynamic motion response data, is plotted over time. The dynamic motion response data includes dynamic displacement data of the brake rotor 20. When plotted over time, a 3D dynamic displacement for the brake rotor 20 movement is obtained.

The high speed camera 10 may be controlled and operated by a computer to take the pictures of the brake rotor. The computer may include software stored in a memory which controls the taking of the pictures and processes the resulting data, i.e., the dynamic motion response data, to obtain a 3D dynamic motion analysis. The high speed camera 10 may include hardware and software used for operations such as taking, storing, and/or processing a picture or pictures. For example, certain software systems, such as PONTOS, ARAMIS, and VIC-3D along with camera hardware systems such as PHANTOM series from Vision Research, Inc., and FASTCAM series from Photron, Inc., may be modified to take the pictures and process a the resulting data to obtain the 3D dynamic motion analysis.

Figure 8:
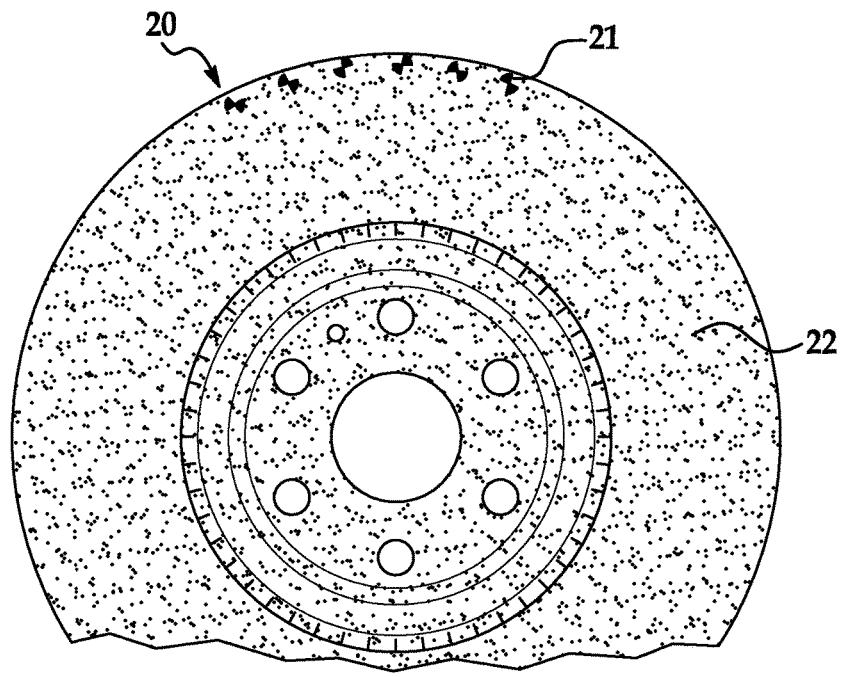
FIG. 8 illustrates an example of a rotor with speckle pattern and markers applied.

In one non-limiting embodiment, for example as shown in FIG. 8, markers 21 and/or speckle patterns 22 are placed on the brake rotor 20 to locate the different points as on the brake rotor 20 as the brake rotor 20 moves. In another non-limiting embodiment, a light shade may be projected to locate different points on the brake rotor 20 as the brake rotor moves.

In the present invention, the use of a high speed camera, or cameras 10, replaces the need to position a microphone, accelerometer or other sensor near the brake rotor. The use of cameras 10 to record movement of the brake rotor 20, instead of accelerometers, microphones or other sensors, may reduce or eliminate multiple impacts and measurements that are required in conventional systems As such, the present invention may be more practical for a production environment use.

Figure 4:
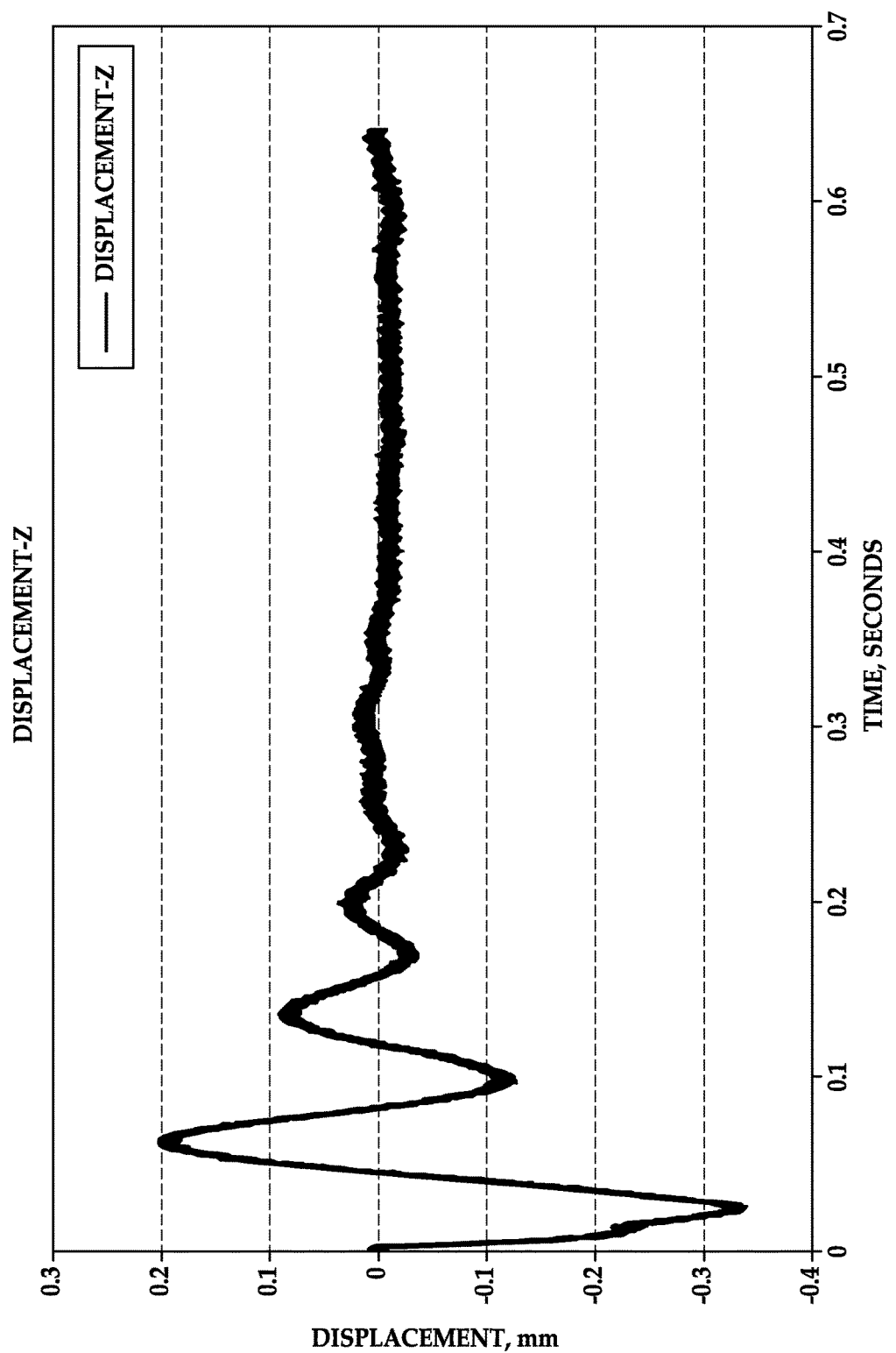
FIG. 4 illustrates a graph representing an example of displacement output generated by a digital image correlation system.

In operation, the following steps provide one example of how the damping may be measured, by calculating the Q factor and/or damping factor:

Place Brake Rotor 10 on a support 25.
Position the high-speed camera or cameras 10 proximate to the brake rotor 20 to photograph the brake rotor 20, for example, as shown in FIG. 1.
Excite the brake rotor 20 using the impulse hammer 30 or other excitation device. In an exemplary embodiment, the excitation device is fitted with a force transducer.
Record the dynamic response, for example the displacement response time history, of the brake rotor for a predetermined amount of time, for example, as shown in FIG. 4.
Extract the displacement response time history of selected points on the surface of the brake rotor 20. Velocity and acceleration extracted from the software or calculated from the recorded displacements may also be used for further processing.
Determine the frequency of the selected vibration modes. In an exemplary embodiment, a Fast Fourier Transform (FFT) method is used.
Apply a filter on the time data to extract the response of the frequencies and modes and operating deflection shapes used for the damping factor and Q factor calculations.
Calculate the damping factor and the Q factor of any, some or all points.

In an exemplary embodiment, the damping factor and Q factor of any, some or all points may be calculated using one of following techniques:

a) Time domain logarithmic decrement method: Using this method, dynamic motion response data includes a decay rate of the dynamic response calculated from the time history. The Q factor and the damping factor is calculated from the dynamic response. This method is further described below.

b) Time domain envelope and decay constant calculation using Hilbert transform: In this method, an envelope of the time signal is calculated for a sinusoidal signal using a Hilbert transform and the decay rate. Q factor and damping factor are calculated is calculated from that result. This method is further described below.

c) Extract the frequency response function of the output using Fast Fourier Transform and determine modal damping factor and modal Q factor using the 3dB method which is described below. A variation of the 3dB method, called the ndB method, may be used instead, where "n" is any number or fraction.

d) Extract the frequency response of the output using FFT and determine the damping factor and Q factor using a modal curve-fitting algorithm/program. In a modal curve-fitting process, a theoretical curve is fit to match the measured Frequency Response Function (FRF) and the frequency, damping and mode shape are estimated. The dynamic response from an operational condition can be used instead of an external excitation of the work piece and damping obtained using the response or through an operational modal analysis.

e) Power Input Method (PIM): This method is based on a comparison of dissipated energy of a system to its maximum strain energy under steady state vibration, which provides frequency-averaged damping values, similar to those discussed in B. Bloss, M.D. Rao, Measurement of Damping in Structures by the Power Input Method, Experimental Techniques Volume 26, Issue 3, Pages 30-32, May 2002.

In addition to the above methods, a standard method such as a ASTM method may be applied using a test specimen instead of a brake rotor. It is understood that the above techniques are non-limiting examples of how the damping may be measured using the system described herein. Other suitable methods of calculation may be used as well.

Figure 2:
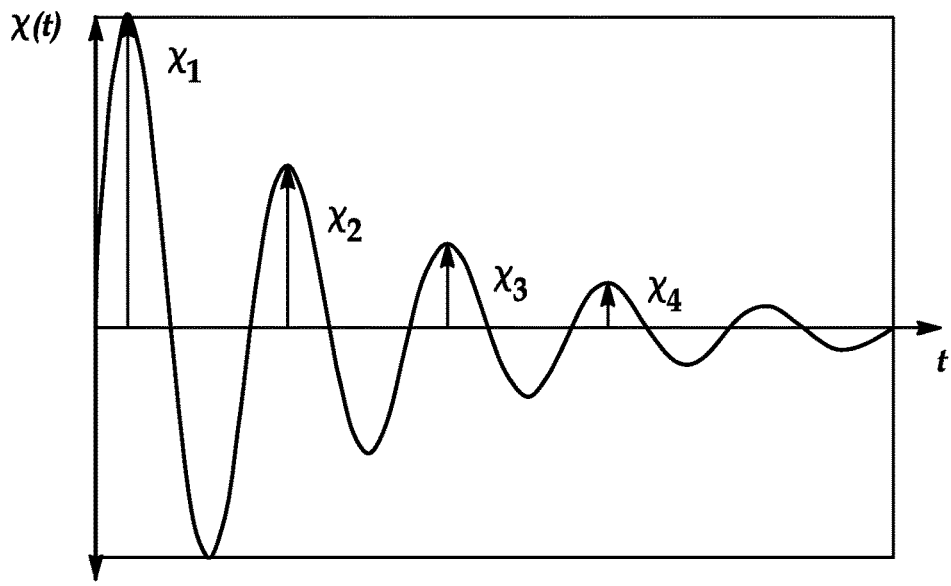
FIG. 2 illustrates a graph representing an example of a logarithmic decrement method of measuring damping factor and Q factor in accordance with the invention.

In the Time domain logarithmic decrement method described above, the free vibration displacement amplitude history of a system to an impulse is measured. A free decay curve is generated, as shown in FIG. 2. The logarithmic decrement is the natural logarithmic value of the ratio of two adjacent peak values of displacement in free decay vibration as shown in FIG. 2.

Figure 3:
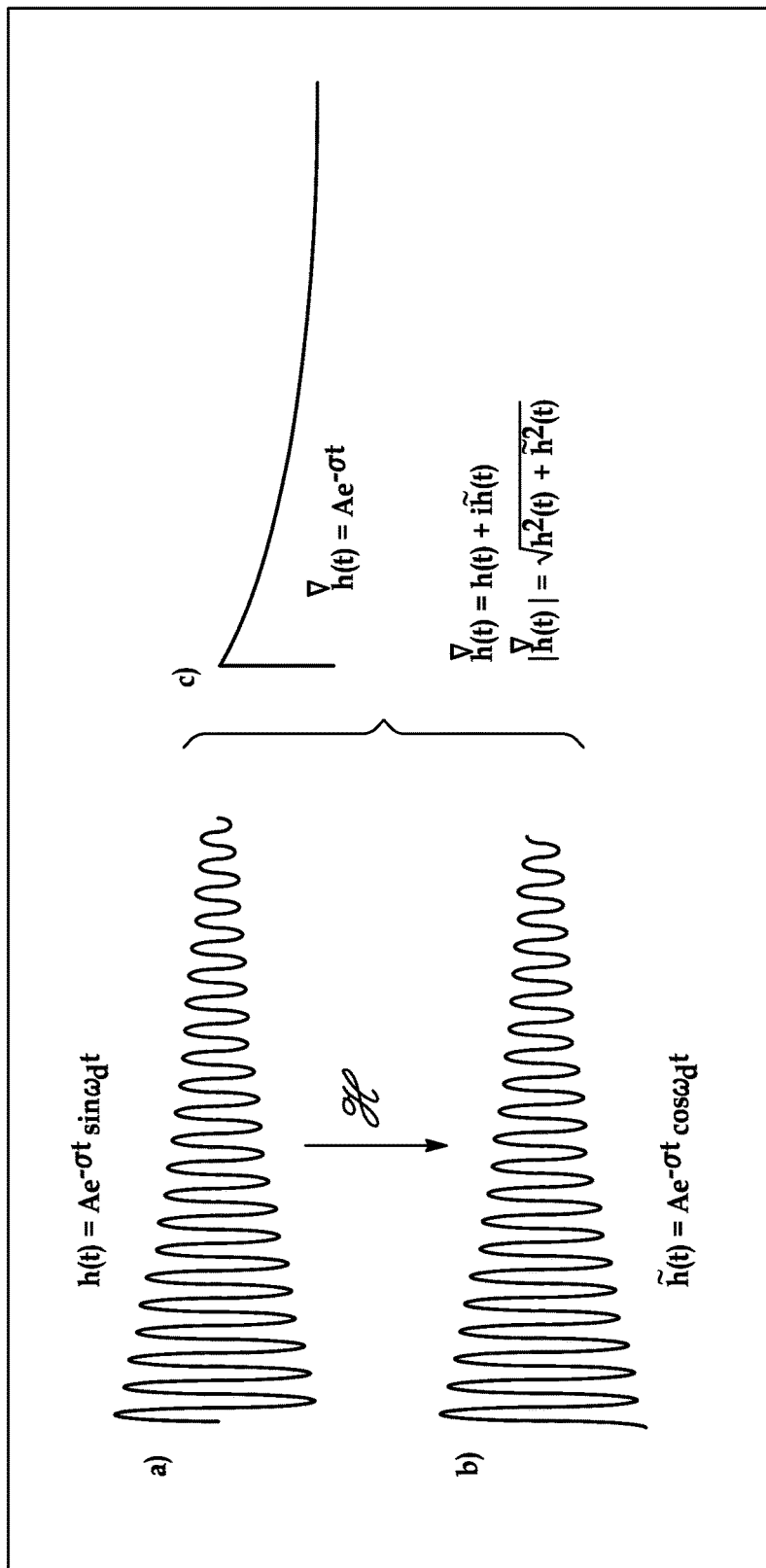
FIG. 3 illustrates graphs representing examples of a Q factor calculation using the time domain envelope decay method.

In the time domain envelope decay calculation, the signal is first filtered to extract the frequency of interest. Then, the envelope of the sinusoidal signal is extracted using a Hilbert transform. The resulting signal may be plotted on a log scale and the decay rate may be obtained from there. An example of this process is shown in FIG. 3.

A modal Q factor may be determined where the damping in the brake rotor 20 is a measure of the rate at which the energy is dissipated when the vibration response decays. The modal Q factor compares the frequency at which a system oscillates to the rate at which it dissipates its energy. A higher modal Q factor indicates a lower rate of energy dissipation relative to the oscillation frequency. The modal Q factor may be calculated by applying an impact force to the brake rotor 20 and measuring the frequency response function (FRF) of the dynamic response. That is, the modal Q factor is a specific case of the Q factor discussed above that is calculated by measuring the FRF of the dynamic response.

Figure 5:
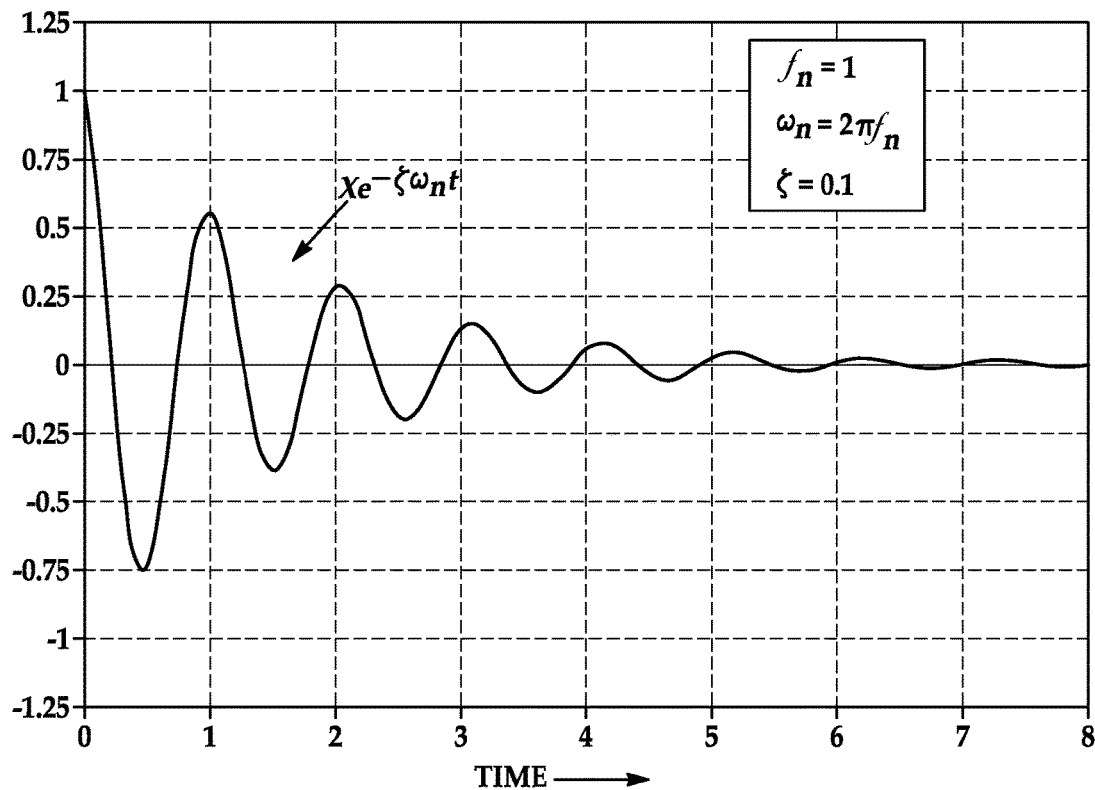
FIG. 5 illustrates a graph representing a quantified example of the decay of the response plotted over time.

FIG. 5 shows the decay of the response plotted over time. Since power and energy are proportional to the square of the amplitude of the oscillation, the bandwidth on an amplitude-frequency graph may be measured to $1/\sqrt{2}$ of the peak or approximately −3 db.

Figure 6:
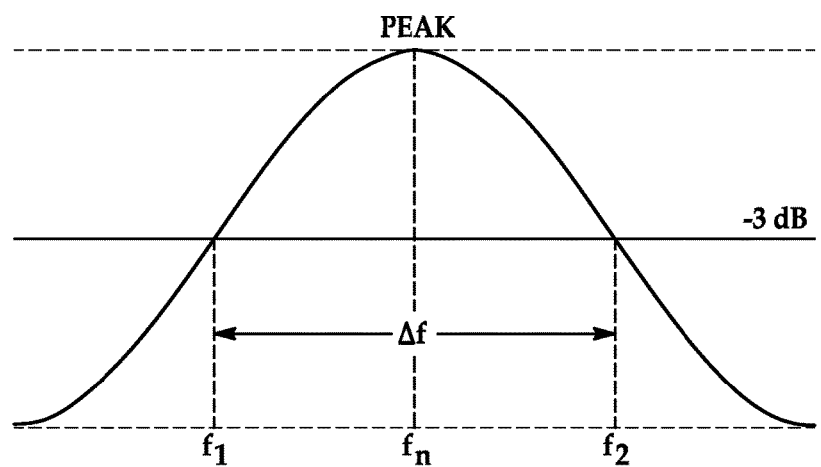
FIG. 6 illustrates a graph representing an example of a response peak and parameters used to calculate a Q factor.
Figure 7:
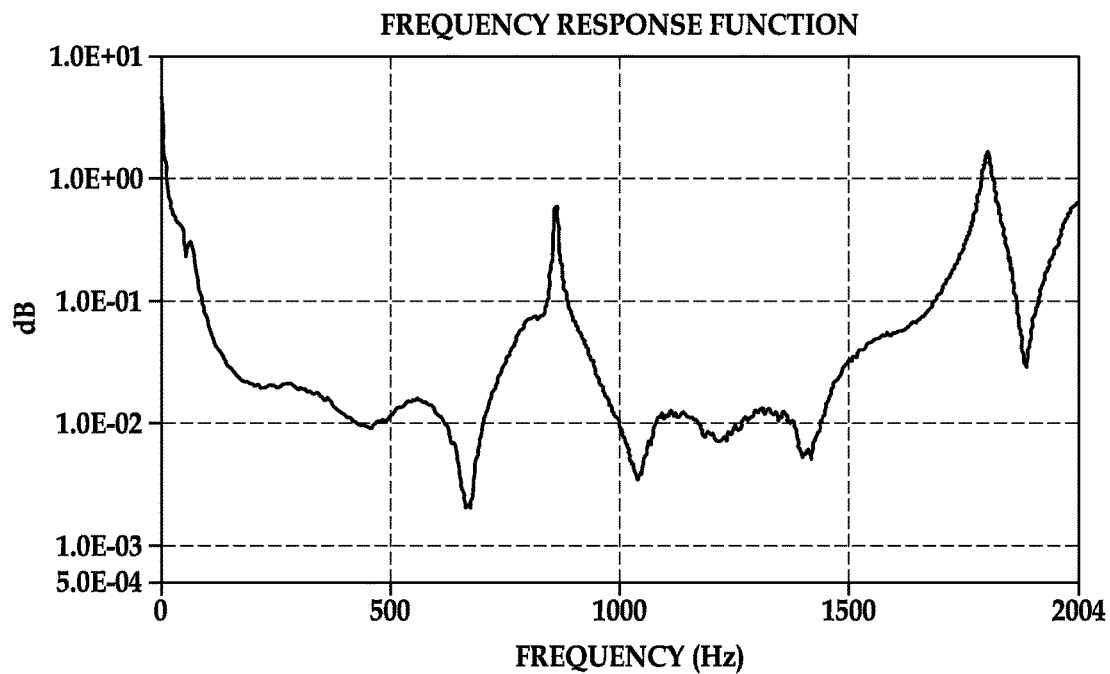
FIG. 7 illustrates a graph representing an example of a frequency response function (FRF) from which a Q factor may be calculated.

FIG. 6 shows the response peak and the parameters used to calculate Q factor. As can be seen in FIG. 6, "fn" is the natural frequency and f1 and f2 are the frequencies at 3 dB drop in the amplitude of the frequency response function (FRF). The width of the peak in relation to the frequency of the peak determines the Q factor $$Q = \frac{fn}{(f1 - f2)}$$

and damping factor in the brake rotor 20. As can be seen, the higher the difference between f1 and f2, the wider the peak and the more damping in the part. FIG. 7 shows an example of a frequency response function (FRF) from which the Q factor is calculated.

A modal damping factor or modal damping ratio is the ratio of the damping in the brake rotor 20 to a critical damping value. The critical damping value is the value at which there is no oscillation and the amplitude dies down without going through any oscillation. For example:

$$\text{Damping factor } v = c/cc = \frac{c}{2\sqrt{K} \cdot \sqrt{M}}$$

where $cc = 2\sqrt{K.M}$ is the critical damping value;
K is the stiffness; M is the mass; and c is the damping constant which is mathematically represented as the ratio of damping force to the velocity, which is an inherent property of a material.

Damping factor is related to the Q factor by the following formula:

$$v = \frac{1}{2Q}$$

or may be represented as a percentage by:

$$v = \frac{100}{2Q}$$

Hence, Q factor can be represented as:

$$Q = \sqrt{K} \cdot \sqrt{M}$$

where K is the stiffness, M is the mass and c is the damping constant.

The methods described above link two processes: an optical imaging system to output dynamic motion response data, and using the data to obtain a damping factor and a Q factor. This includes processes that may be referred to as digital image correlation and dynamic photogrammetry.

The methods above may provide an advantage over conventional methods in that the response of the whole work piece is recorded at once instead of exciting the work piece and measuring the response of different points on the rotor at different times. The above methods allow for the Q factor and damping factor of any point on the work piece to be extracted in one measurement, the measurement time only varying depending on the required resolution of the measurement.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description.

Having thus described the invention, it is claimed:

1. A method of measuring damping of a work piece comprising:
    placing a work piece on a support;
    placing a plurality of markers at a plurality of locations on the work piece to locate different points as on the work piece as the work piece moves;
    placing a high-speed camera to view the work piece;
    exciting the work piece with an excitation device by physically striking the work piece at any location of the work piece;
    recording a displacement time history of the work piece for a predetermined amount of time;
    extracting a displacement response time history of selected points on a surface of the work piece;
    determining a frequency of selected vibration modes;
    applying a filter on the displacement response time history to extract a response of operating deflection shapes or modes used for a damping factor and a Q factor calculation, the response of any point of the work piece being measured in a single measurement operation; and
    calculating a damping factor and a Q factor.

2. The method of claim 1, wherein the work piece is a brake rotor.

3. The method of claim 1, wherein the work piece is a brake drum.

4. The method of claim 1, including fitting said excitation device with a force transducer.

5. The method of claim 1, wherein the excitation device is an impulse hammer.

6. The method of claim 1, wherein the excitation device is a shaker.

7. The method of claim 1, further comprising calculating velocity and acceleration based on the displace response time history.

\* \* \* \* \*